United States Patent
Keung

(10) Patent No.: US 9,636,432 B2
(45) Date of Patent: May 2, 2017

(54) AIR PURIFICATION UNIT

(71) Applicant: Nano and Advanced Materials Institute Limited, Hong Kong (HK)

(72) Inventor: Lok Hang Keung, Hong Kong (HK)

(73) Assignee: NANO AND ADVANCED MATERIALS INSTITUTE LIMITED, Hong Kong (HK)

( * ) Notice: Subject to any disclaimer, the term of this patent is extended or adjusted under 35 U.S.C. 154(b) by 128 days.

(21) Appl. No.: 14/166,866

(22) Filed: Jan. 29, 2014

(65) Prior Publication Data
US 2014/0294679 A1 Oct. 2, 2014

Related U.S. Application Data

(60) Provisional application No. 61/853,040, filed on Mar. 27, 2013.

(51) Int. Cl.
*A61L 9/20* (2006.01)
*B01D 53/86* (2006.01)
*B01D 53/88* (2006.01)

(52) U.S. Cl.
CPC .......... *A61L 9/205* (2013.01); *B01D 53/8687* (2013.01); *B01D 53/885* (2013.01); *B01D 2255/20707* (2013.01); *B01D 2255/802* (2013.01); *B01D 2257/708* (2013.01); *B01D 2258/06* (2013.01); *B01D 2259/804* (2013.01)

(58) Field of Classification Search
CPC .............................. B01D 53/8687; A61L 9/205
USPC ......................................................... 422/121
See application file for complete search history.

(56) References Cited

U.S. PATENT DOCUMENTS

| 5,933,702 A | 8/1999 | Goswami |
| 2004/0238344 A1 | 12/2004 | Benoit et al. |
| 2005/0186124 A1* | 8/2005 | Fink et al. .................... 422/121 |
| 2007/0107597 A1* | 5/2007 | Cheung ............................. 96/16 |
| 2010/0135864 A1* | 6/2010 | Taniguchi et al. ............. 422/121 |
| 2011/0150720 A1 | 6/2011 | Garfield et al. |
| 2011/0171080 A1* | 7/2011 | Lo ........................... A61L 2/088 422/186.3 |

(Continued)

FOREIGN PATENT DOCUMENTS

| CN | 2787214 Y | 6/2006 |
| CN | 102092812 A | 6/2011 |

OTHER PUBLICATIONS

Luckiesh et al., Transmittance and Reflectance of Germicical (2537) Energy, Apr. 1946, Journal of the Optical Society of America, vol. 36, No. 4.*

(Continued)

*Primary Examiner* — Kevin Joyner
*Assistant Examiner* — Holly Mull
(74) *Attorney, Agent, or Firm* — Spruson & Ferguson (Hong Kong) Limited

(57) ABSTRACT

The presently claimed invention provides a photocatalytic air purification unit, comprising a fin structure and an UV lamp. The fin structure comprises a plurality of fins coated with a layer of photocatalyst, and said fin structure is able to increase the surface area for photocatalyst coating, ultimately increasing air pollutant removal efficiency with minimum air resistance. The air purification unit of the present invention is preferably installed in a HVAC system.

4 Claims, 15 Drawing Sheets

(56) References Cited

U.S. PATENT DOCUMENTS

2012/0080107 A1* 4/2012 Kruglick ................ A61L 9/205
                                                        137/565.01
2013/0052113 A1   2/2013 Molins et al.

OTHER PUBLICATIONS

First Office Action with Search Report of CN201410088422.9 issued by the State Intellectual Property Office of China on Sep. 6, 2015.

* cited by examiner

AIR PURIFICATION UNIT

CROSS REFERENCE TO RELATED APPLICATION

Pursuant to 35 U.S.C. §119(e), this is a non-provisional patent application which claims benefit from U.S. provisional patent application Ser. No. 61/853,040 filed Mar. 27, 2013, and the disclosure of which is incorporated herein by reference.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to an air purification unit, and particularly relates to an air purification unit with photocatalyst.

BACKGROUND

It is well known in the art that when titanium dioxide is exposed to light, a photocatalytic reaction takes place, and such reaction is able to decompose volatile organic compounds or other gaseous pollutants. Thus, photocatalyst is frequently applied to air purification system in order to remove gaseous pollutants, and improve indoor air quality.

In building circulating systems, pollutants from various sources contribute to indoor air pollution, which poses a significant risk towards human health. Illnesses resulting from such indoor pollutants are generally known as the "sick building syndrome." Therefore, in many heating, ventilation, and air conditioning (HVAC) systems, air purification systems are installed so as to remove air pollutants. Particularly, photocatalytic air purification systems are frequently used.

US2004/0238344 discloses an air purification system using excimer lamps for ultra-violet photocatalytic oxidation, and such air purification system can be used in HVAC system. Comparing to conventional low-pressure mercury lamps, the excimer lamps can provide UV radiation with desirable range of wavelength, thereby increasing the efficiency of the photocatalytic reaction. However, the implementation of the excimer lamps increases substantially the cost of the system.

US2011/0150720 provides an air filtration system and a method for making a photocatalytic oxidation substrate by coating a photocatalyst onto a metal substrate. However, the amount of the photocatalyst coated on the metal substrate is limited, resulting in low air pollutant removal efficiency.

US2013/0052113 relates to a method and a device for the purification of air by passing a flow of the air through a filter having a photocatalytic action subjected to UV lighting. The filter comprises a felt of mineral fibers, the fibers of which are coated with a material having a photocatalytic action, the residence time of the air in contact with the filter is greater than 70 msec and the UV lighting has a power of less than 35 mW per cm$^2$ of lit surface of filter having a photocatalytic action. Nevertheless, the felt induces high air resistance, leading to high loading of the air flow generation unit.

According to an example in a prior art, FIG. 1 shows a cylindrical metal substrate coated with photocatalyst of an air purification unit. An UV lamp is installed along the axis of the metal substrate. The holes on the metal substrate are used for allowing air to pass through. Nevertheless, the performance of air pollutant removal is not effective since only limited amount of photocatalyst is coated on the metal substrate.

Consequently, there is an unmet need for a photocatalytic air purification system that can generate efficient air pollutant removal rate with minimal air resistance.

SUMMARY OF THE INVENTION

Accordingly, the presently claimed invention is to provide an air purification unit.

In accordance with an embodiment of the presently claimed invention, the air purification unit comprises a fin structure and an UV lamp. The fin structure comprises a plurality of fins and a fin holder. The fins are attached on to the fin holder, which is used to fix the positions of the fins. Surfaces of the fins are coated with a photocatalyst layer, and are irradiated by the UV light from the UV lamp. The fins are separated from each other by empty spaces for allowing air to pass through.

Unlike the traditional air purification system, the air purification unit of the presently claimed invention provides several advantages. The fin structure is able to increase the surface area for depositing photocatalyst, the contact area between air pollutants in the airflow and the photocatalyst, as well as the irradiation area irradiated by the UV light from the UV lamp, thereby enhancing the photocatalytic oxidation and improving air pollutant removal efficiency.

Meanwhile, the fin structure provides empty spaces for air to pass through, thus preventing the fin structure from inducing large air resistance. The fin density of the fin structure is preferably 1-2 fins/cm, which optimizes the performance of the air purification unit with the balance of trade offs between the air flow rate and the air pollutant removal efficiency.

BRIEF DESCRIPTION OF THE DRAWINGS

Embodiments of the present invention are described in more detail hereinafter with reference to the drawings, in which.

DETAILED DESCRIPTION OF PREFERRED EMBODIMENTS

In the following description, air purification units, and the fin structures of said air purification units are set forth as preferred examples. It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

Figure 2:
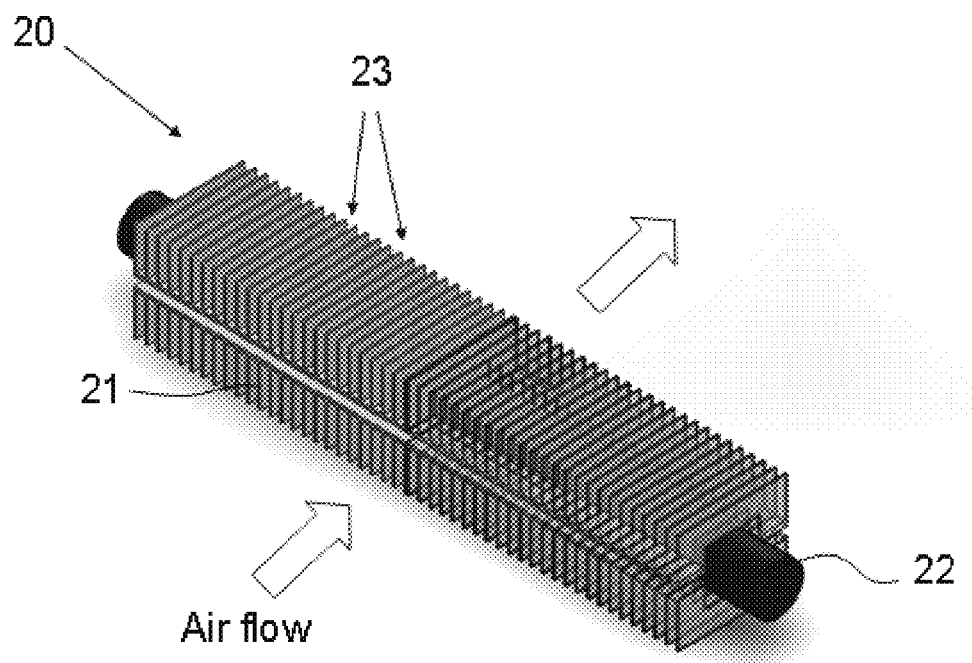
FIG. 2 is a perspective view of an air purification unit with a fin structure having a rectangular shape according to an embodiment of the presently claimed invention.
Figure 2A:
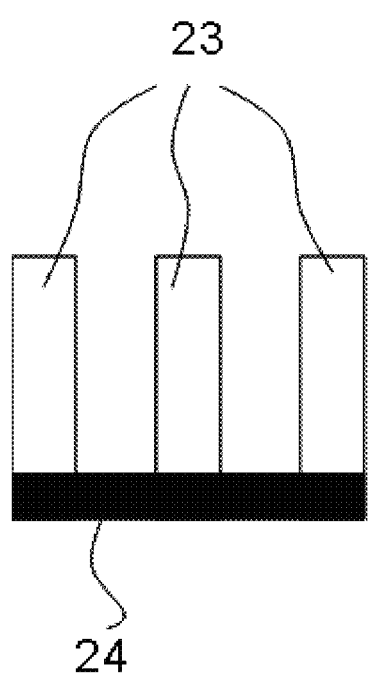
FIG. 2A is a partial enlargement view of the air purification unit of FIG. 2.
Figure 3A:
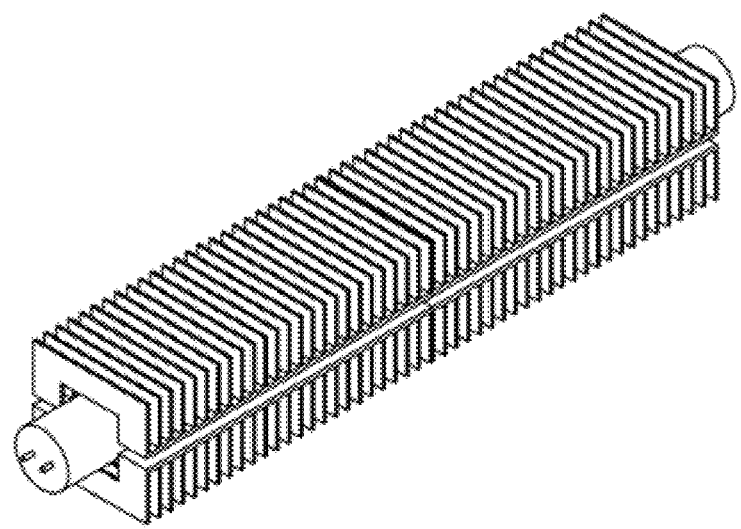
FIG. 3A-E are a perspective view, a front view, a bottom view, a left view, and a partial enlargement view respectively of an air purification unit with a fin structure having a rectangular shape according to another embodiment of the presently claimed invention.
Figure 3B:
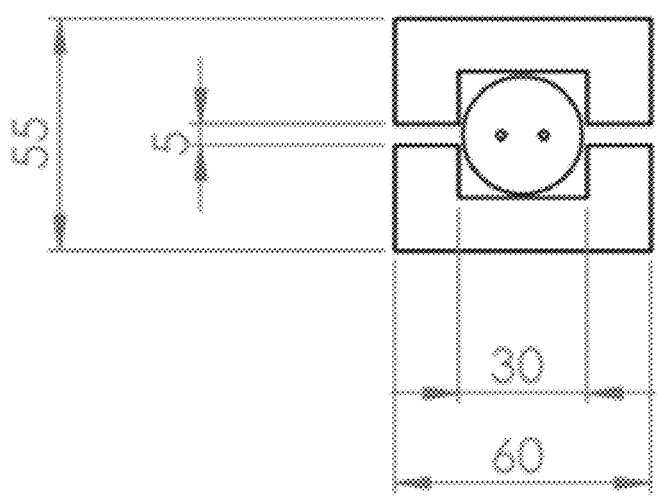
Figure 3C:
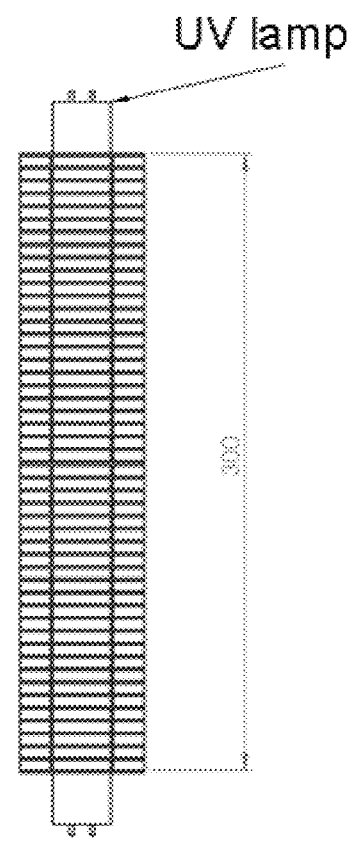
Figure 3D:
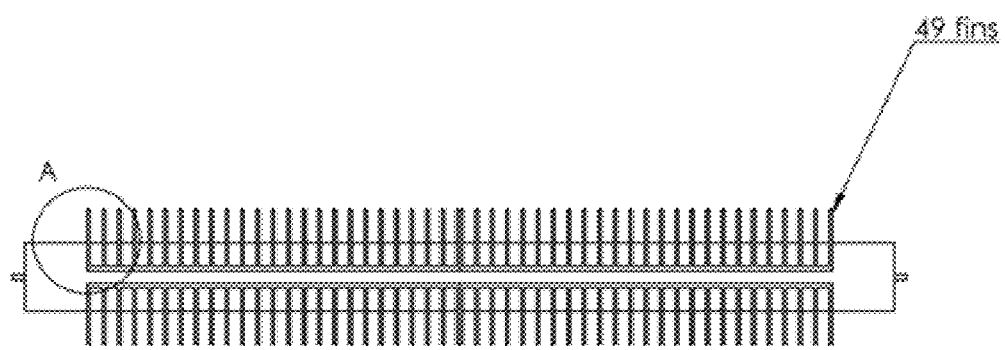
Figure 3E:
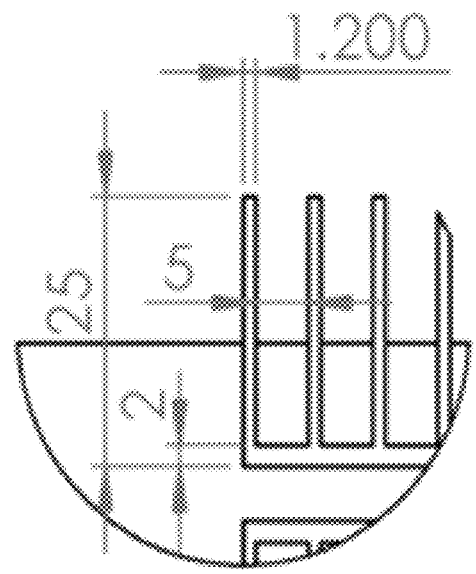

FIG. 2 is a perspective view of an air purification unit with a fin structure having a rectangular shape according to an embodiment of the presently claimed invention. The air purification unit 20 comprises a fin structure 21 and an UV lamp 22. The UV lamp 22 is located along the axis of the fin structure 21, and enclosed by the fin structure 21. The fin structure 21 is rectangular in shape, and comprises a plurality of fins 23 and a fin holder 24 (as shown in the partial enlargement view of FIG. 2A). The fins 23 are attached on to the fin holder 24, which is used to fix the positions of the fins 23. The fins 23 are positioned in parallel with each other, and separated from each other by empty spaces for allowing air to pass through. Surfaces of the fins 23 are coated with a layer of photocatalyst, and are irradiated by the UV light from the UV lamp 22. The fin structure 21 is placed in a direction that the flat surfaces of the fins 23 are substantially in parallel with the air flow direction as indicated by the arrows.

When the air flow passes through the fin structure, air pollutants in the air flow are in contact, or are adsorbed on the photocatalyst. Under the irradiation of the UV light on the photocatalyst, photocatalytic reaction occurs, in which the photocatalyst generates electron-hole pair, producing free radicals to decompose the air pollutants.

As the fin structure provides a large amount of surface area coated with the photocatalyst, the air pollutant removal rate can be highly enhanced due to the increased contact area between the air pollutants and the photocatalyst, as well as the increased irradiation area irradiated by the UV lamp. Meanwhile, there are empty spaces for the air to pass through the fin structure, so the fin structure merely induces a slight amount of air resistance to attenuate the air flow, ultimately relieving the burden of the air flow generating unit, and reducing the power consumption for air flow generation.

FIG. 3A-E are a perspective view, a front view, a bottom view, a left view, and a partial enlargement view respectively of an air purification unit with a fin structure having a rectangular shape according to another embodiment of the presently claimed invention. The UV lamp is 30 mm in diameter. The fin structure is 300 mm in length, 55 mm in height, 60 mm in width, and comprises 49 fins. Each of the fins is 1.2 mm in thickness, and is separated from each other by 5 mm. The fin holder is 2 mm in thickness. The fin density of the fin structure is approximately 1.6 fins/cm. The total surface area provided for photocatalyst coating is approximately 2610 $cm^2$.

Figure 4:
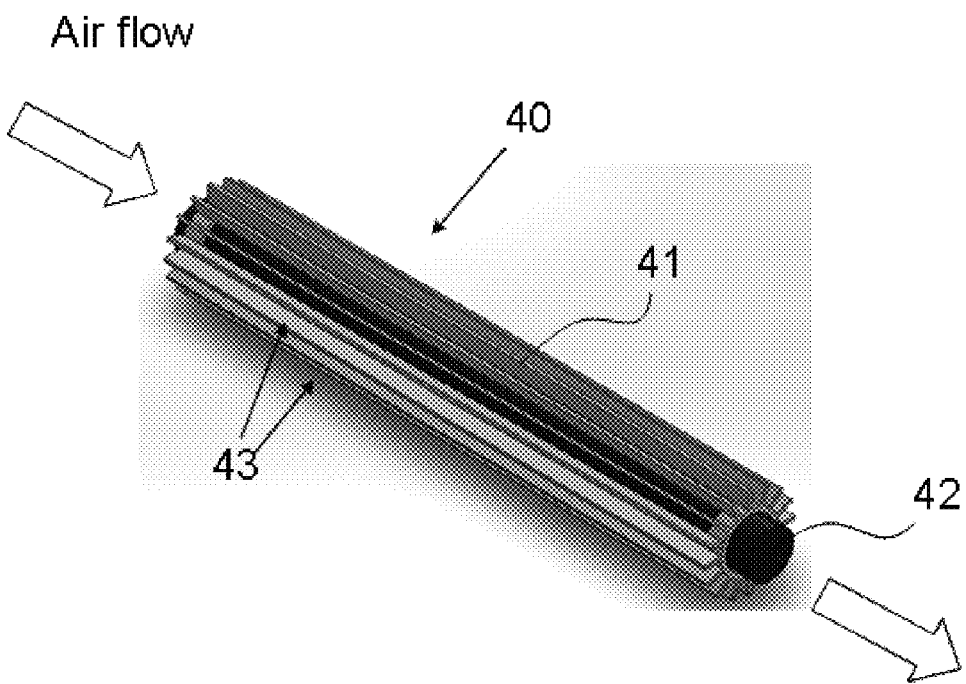
FIG. 4 is a perspective view of an air purification unit with a fin structure having a cylindrical shape according to an embodiment of the presently claimed invention.
Figure 4A:
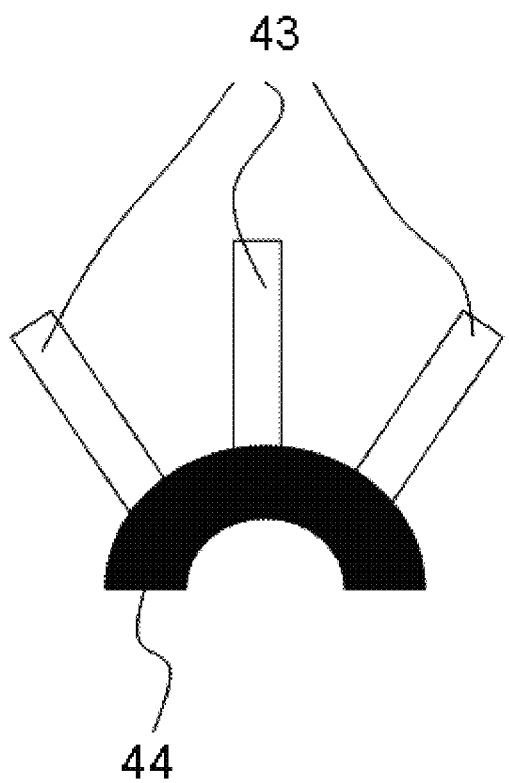
FIG. 4A is a partial enlargement view of the air purification unit of FIG. 4.
Figure 5A:
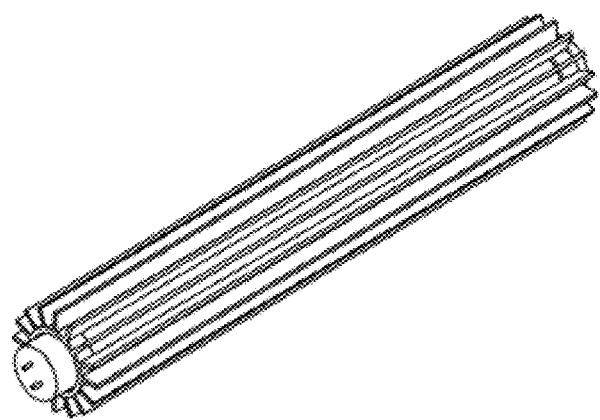
FIG. 5A-E are a perspective view, a front view, a bottom view, a left view, and a partial enlargement view respectively of an air purification unit with a fin structure having a cylindrical shape according to another embodiment of the presently claimed invention.
Figure 5B:
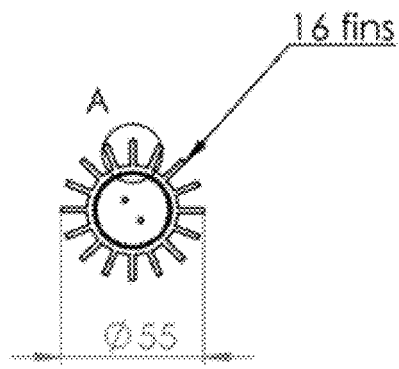
Figure 5C:
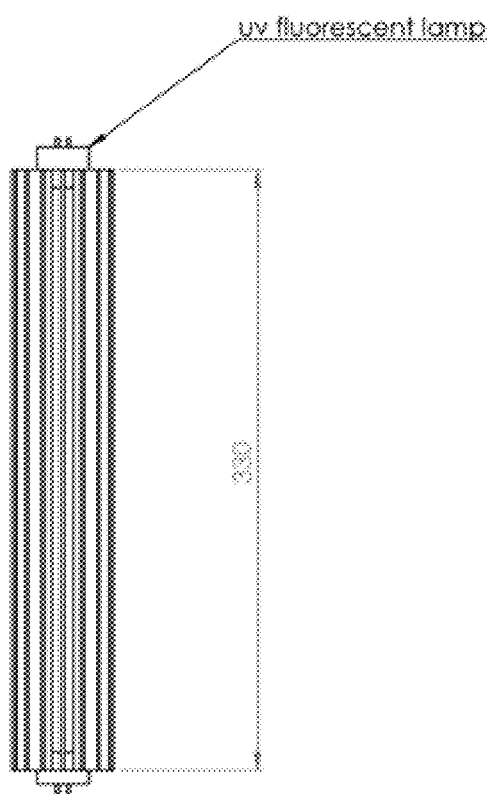
Figure 5D:
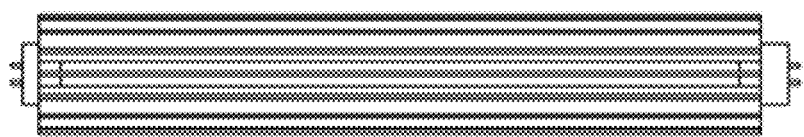
Figure 5E:
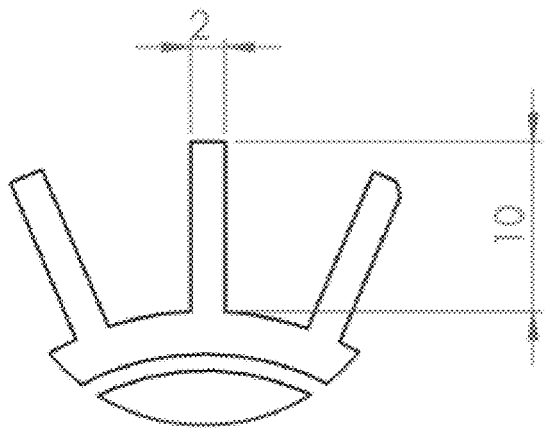

FIG. 4 is a perspective view of an air purification unit with a fin structure having a cylindrical shape according to an embodiment of the presently claimed invention. The air purification unit 40 comprises a fin structure 41 and an UV lamp 42. The UV lamp 42 is located along the axis of the fin structure 41, and enclosed by the fin structure 41. The fin structure 41 is cylindrical in shape, and comprises a plurality of fins 43 and a fin holder 44 (as shown in the partial enlargement view of FIG. 4A). The fins 43 are attached radially and symmetrically on to the fin holder 44, which is used to fix the positions of the fins 43. The fins 43 are positioned substantially in parallel with each other, and separated from each other by empty spaces to allow air to pass through. The surfaces of the fins 43 are coated with a layer of photocatalyst, and are irradiated by the UV light from the UV lamp 42. The fin structure 41 is placed in a direction that the flat surface of the fins 43 is substantially in parallel with the air flow direction as indicated by the arrows.

FIG. 5A-E are a perspective view, a front view, a bottom view, a left view, and a partial enlargement view respectively of an air purification unit with a fin structure having a cylindrical shape according to another embodiment of the presently claimed invention. The fin structure is 330 mm in length, 55 mm in diameter, and comprises 16 fins. Each of the fins is 2 mm in thickness and 10 mm in width. The fin density of the fin structure is approximately 1.5 fins/cm. The total surface area provided for photocatalyst coating is about 1310 $cm^2$.

Figure 1:
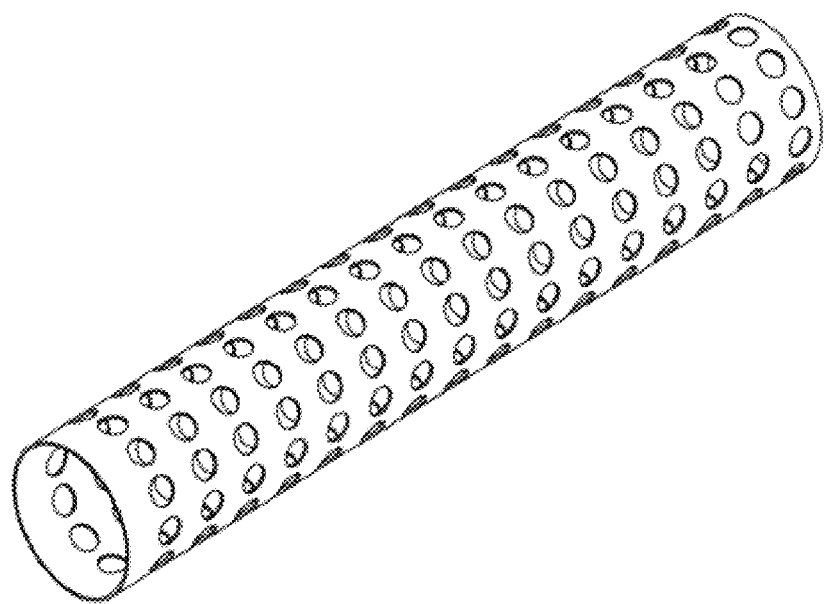
FIG. 1 is a perspective view of a metal substrate coated with photocatalyst of an air purification unit in a prior art.

Comparing to the metal substrate of the prior art as shown in FIG. 1, the fin structures of the present invention as shown in FIGS. 3 and 5 can provide from 3 to 6 times of the surface area for the photocatalyst coating.

Although the air pollutant removal efficiency increases when the number of the fin increases, air resistance of the fin structure increases as well, reducing the air flow rate in the ventilation system. Therefore, to optimize the trade offs between the air pollutant removal efficiency and the air flow rate, a preferable fin density is in the range of 1 to 2 fins/cm. Also, a preferable fin thickness is in the range of 1 to 2 mm. Accordingly, a plurality of the empty spaces can occupy 60%-90% of the cross-sectional area of the fin structure.

Optionally, the fin structure comprises several sub-fin structures, assembled together to form the fin structure. The fin structure can be produced by milling and welding. In addition, the fin structure can be made from metal. Preferably, the fin structure is made from aluminum, copper or iron.

The photocatalyst can be coated on the surface of the fins by methods of dipping or painting, followed by drying for at least 12 hrs at room temperature and curing at 500° C. for 30 mins. Furthermore, the fin holder can be coated with photocatalyst as well. Preferably, the photocatalyst is titanium dioxide ($TiO_2$).

The UV light reflectance of the photocatalyst layer can be in the range of 10 to 42%. As the fins are positioned in substantially parallel with each other, the reflected UV light is able to be further reflected between the fins within the empty space. This reduces UV light loss, and ultimately increases the efficiency of photocatalytic oxidation and lowers the power consumption of the UV lamp.

Figure 6A:
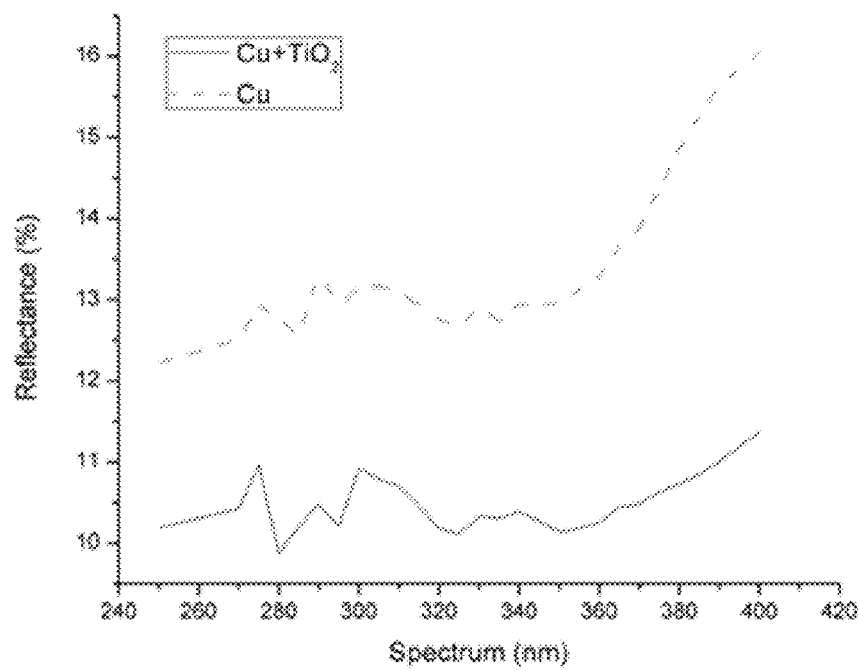
FIG. 6A shows UV light reflectance of a copper fin and a copper fin coated with $TiO_2$ respectively with respect to the wavelengths ranging from 250 to 400 nm according to an embodiment of the presently claimed invention.

FIG. 6A shows UV light reflectance of a copper fin and a copper fin coated with $TiO_2$ respectively with respect to the wavelengths ranging from 250 to 400 nm according to an embodiment of the presently claimed invention. The UV light reflectance of the copper fin ranges from about 12% to about 16% as shown in the dotted line, and the UV light reflectance of the copper fin coated with $TiO_2$ ranges from about 10% to about 11.5% as shown in the solid line. The average UV light reflectance of the copper fin coated with $TiO_2$ is about 10% within the wavelengths in the range of 240 to 280 nm.

Figure 6B:
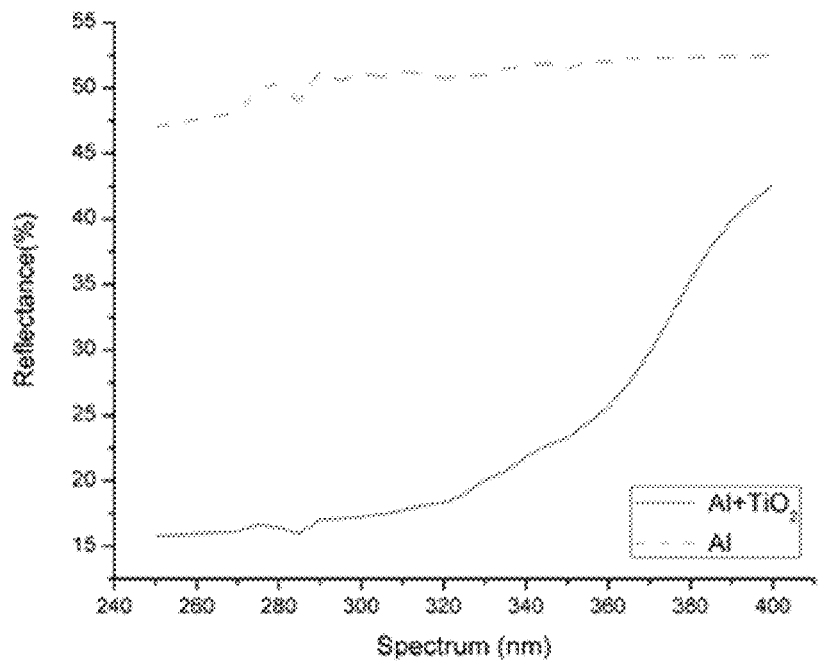
FIG. 6B shows UV light reflectance of an aluminum fin and an aluminum fin coated with $TiO_2$ respectively with respect to the wavelengths ranging from 250 to 400 nm according to an embodiment of the presently claimed invention.

FIG. 6B shows UV light reflectance of an aluminum fin and an aluminum fin coated with $TiO_2$ respectively with respect to the wavelengths ranging from 250 to 400 nm according to an embodiment of the presently claimed invention. The UV light reflectance of the aluminum fin ranges from about 47% to about 53% as shown in the dotted line, and the UV light reflectance of the aluminum fin coated with $TiO_2$ ranges from about 15% to about 42% as shown in the solid line. The average UV light reflectance of the aluminum fin coated with $TiO_2$ is about 15% within the wavelengths in the range of 240 to 280 nm.

The UV light reflectance of the fin coated with photocatalyst can be in the range of 10% to 42%. As ultraviolet C (UVC) is preferably used, the average UV light reflectance of the fin coated with photocatalyst can be in the range of 10 to 15%.

The UV lamp can be a low-pressure mercury lamp or an excimer lamp. The wavelengths of UV light are in the range of 400 to 10 nm. The preferable range of the wavelengths of UV light is from 290 to 100 nm. However, the air purification unit of the present invention is not limited to UV light and UV lamp. Other light sources are applicable in the present invention. Similarly, light with the wavelengths different from that of UV light is also applicable.

In addition, a plurality of air purification units of the present invention can be configured to form an air purification system.

The air pollutants removed by the air purification unit of the present invention can be volatile organic compounds, nitric oxides, or airborne bacteria.

Air resistance simulation tests were conducted with the air purification units of the present invention. Drag coefficients $c_d$ of the air purification units were studied in the test. The drag coefficient is defined as follow:

$$c_d = \frac{2F_d}{\rho v^2 A}$$

where $F_d$ is a drag force, which is a force component in the direction of a flow velocity, $\rho$ is a mass density of a fluid, $v$ is a speed of an object relative to the fluid, and $A$ is a reference area.

In the simulation, the pressure drop ($F_d/A$) and the mass density of air ($\rho$) were kept constant. Therefore, the drag coefficient increases with the decrease of the air flow velocity. Two different inlet and outlet systems were used in the test, including a rectangular inlet and outlet system, and a circular inlet and outlet system. The rectangular inlet and outlet system provides a rectangular inlet to allow air to flow in, and a rectangular area in the outlet to allow air to flow out. The circular inlet and outlet system provides a small circular inlet to allow air to flow in, and a small circular outlet to allow air to flow out. Control experiments were conducted by using the air purification unit of the prior art as shown in FIG. 1.

Figure 7A:
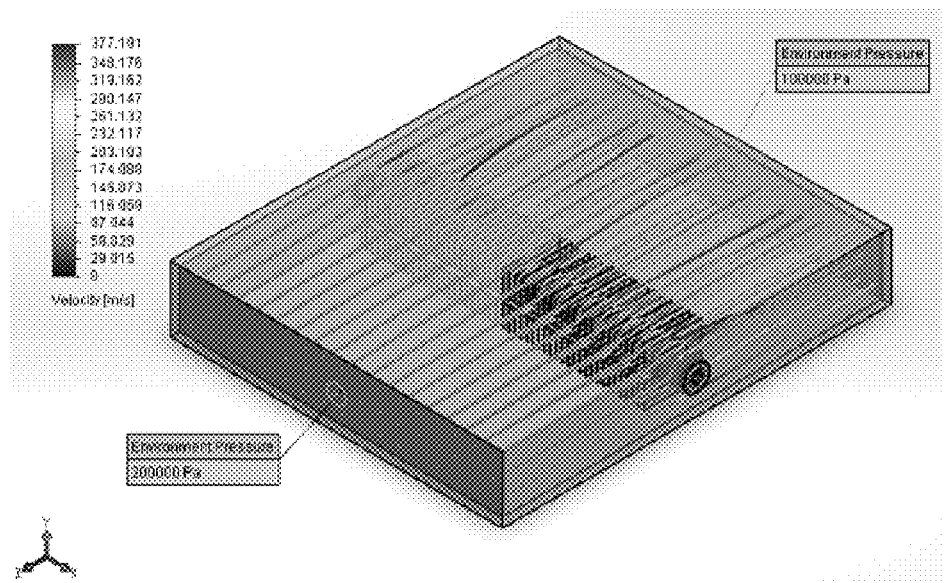
FIGS. 7A and 7B show the air flow simulation results simulated with the air purification unit of FIG. 3 under a rectangular inlet and outlet system and a circular inlet and outlet system respectively.
Figure 7B:
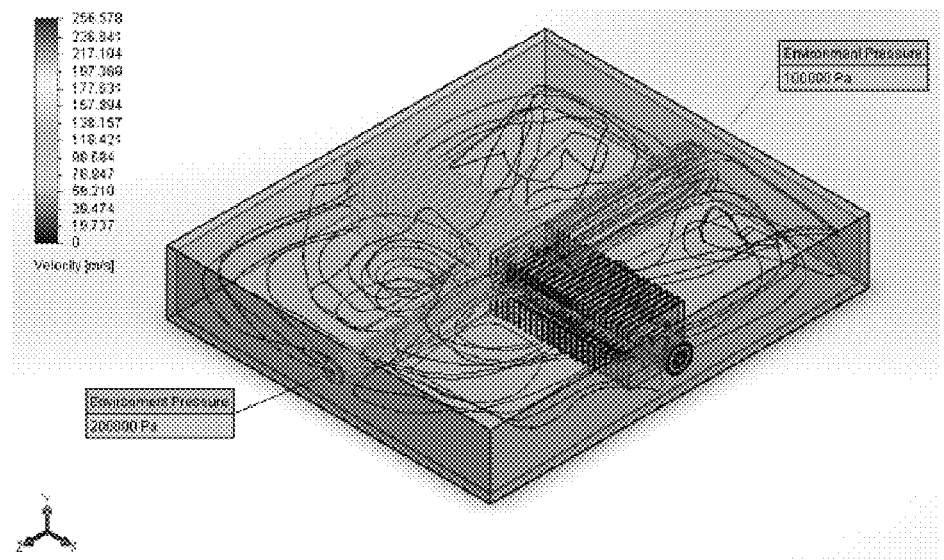

FIGS. 7A and 7B show the air flow simulation results simulated with the air purification unit of FIG. 3 under the rectangular inlet and outlet system and the circular inlet and outlet system respectively. The air purification unit of FIG. 3 was located in the direction perpendicular to the air flow direction.

Figure 7C:
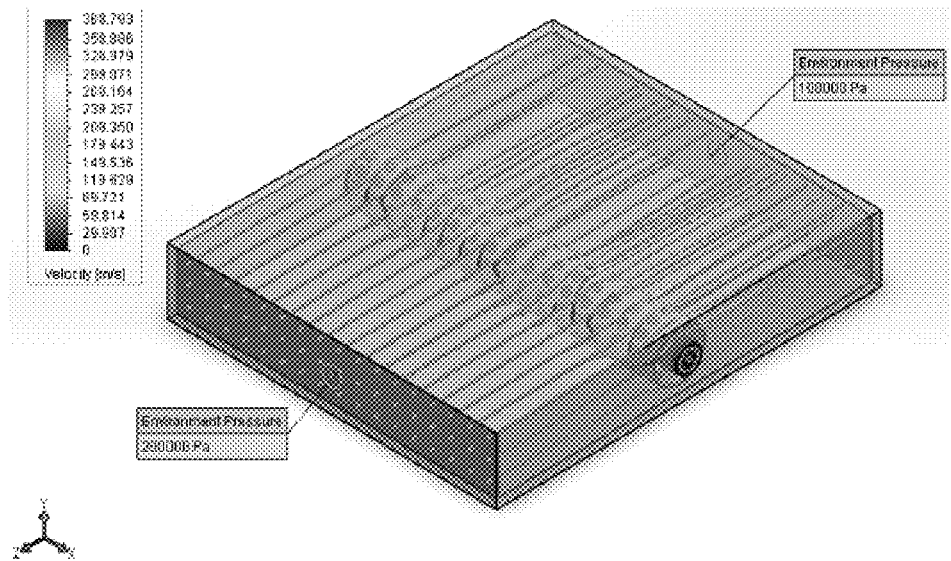
FIGS. 7C and 7D show the air flow simulation results simulated with the air purification unit of FIG. 1 under the rectangular inlet and outlet system and the circular inlet and outlet system respectively.
Figure 7D:
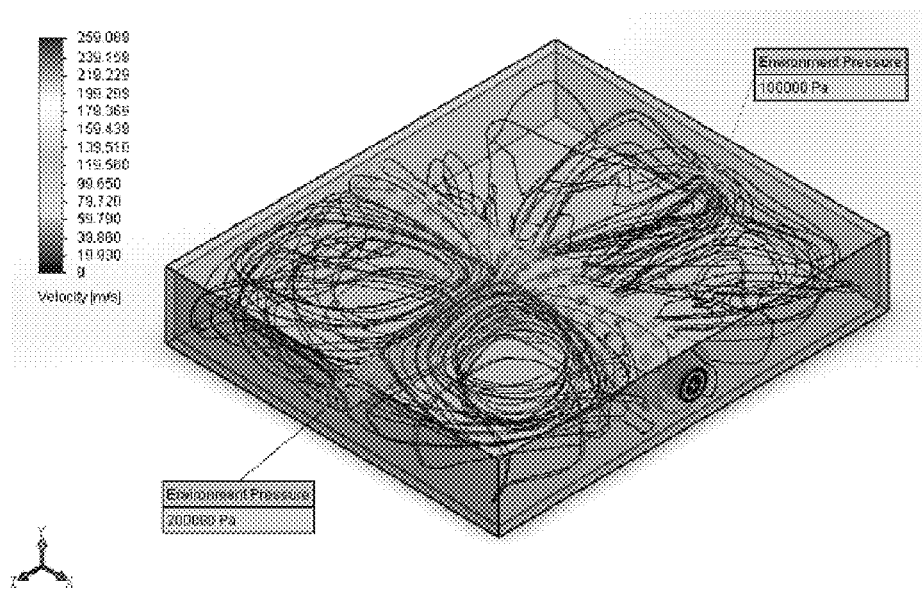

FIGS. 7C and 7D show the air flow simulation results simulated with the air purification unit of FIG. 1 under the rectangular inlet and outlet system and the circular inlet and outlet system respectively. The air purification unit of FIG. 1 was located in the direction perpendicular to the air flow direction.

Figure 7E:
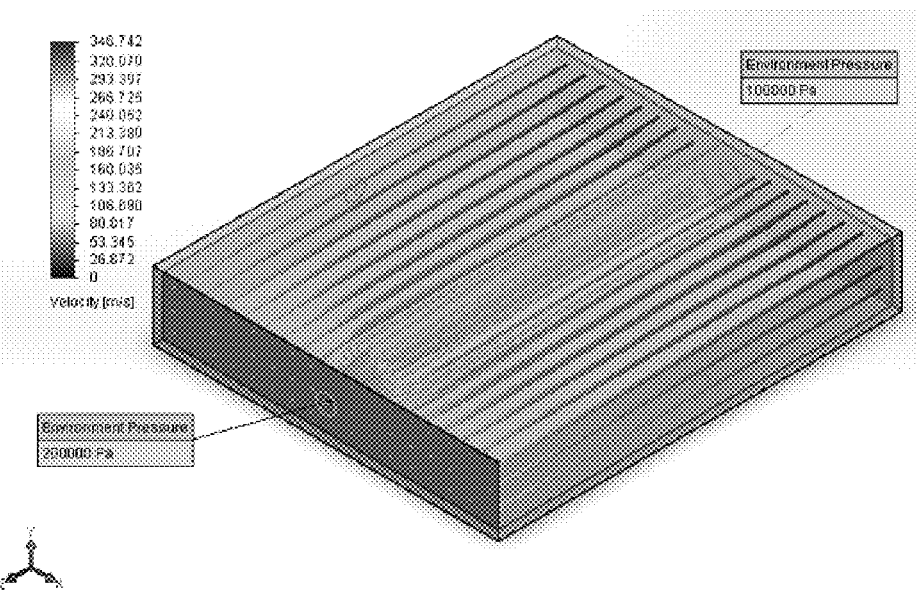
FIGS. 7E and 7F show the air flow simulation results simulated with the air purification of FIG. 5 under the rectangular inlet and outlet system and the circular inlet and outlet system respectively.
Figure 7F:
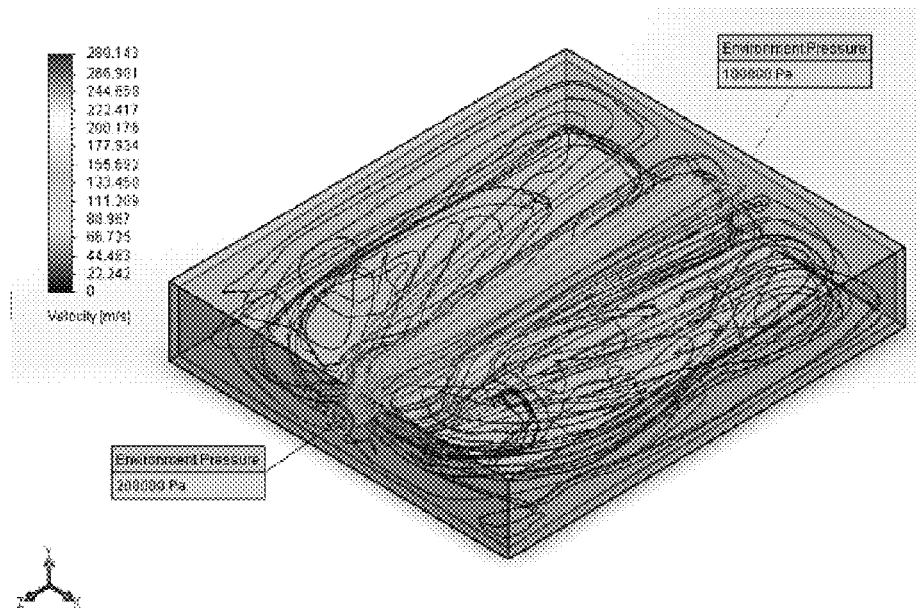

FIGS. 7E and 7F show the air flow simulation results simulated with the air purification of FIG. 5 under the rectangular inlet and outlet system and the circular inlet and outlet system respectively. The air purification unit of FIG. 5 was located in the direction parallel to the air flow direction.

Figure 7G:
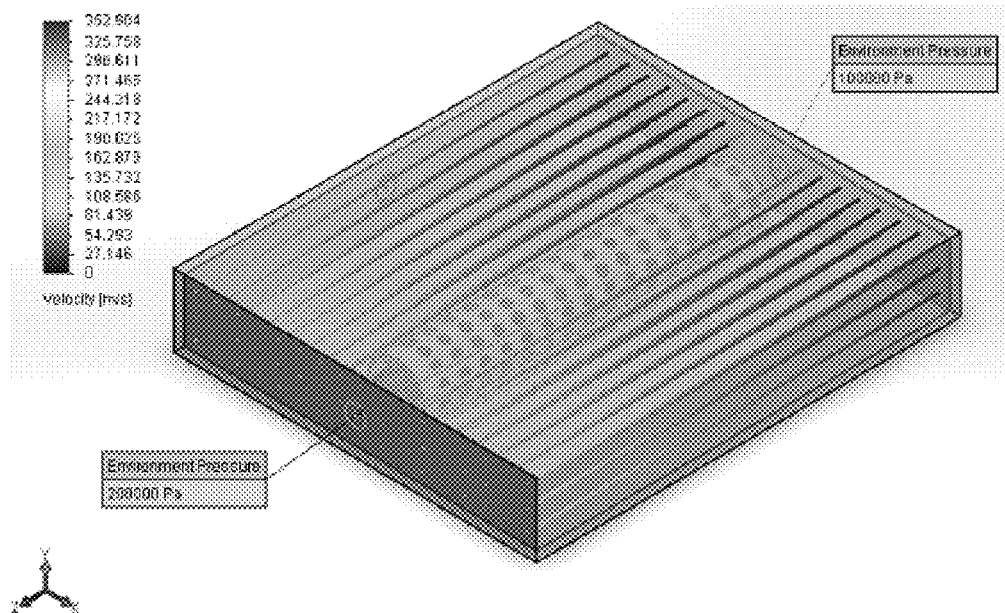
FIGS. 7G and 7H show the air flow simulation results simulated with the air purification unit of FIG. 1 under the rectangular inlet and outlet system and the circular inlet and outlet system respectively.
Figure 7H:
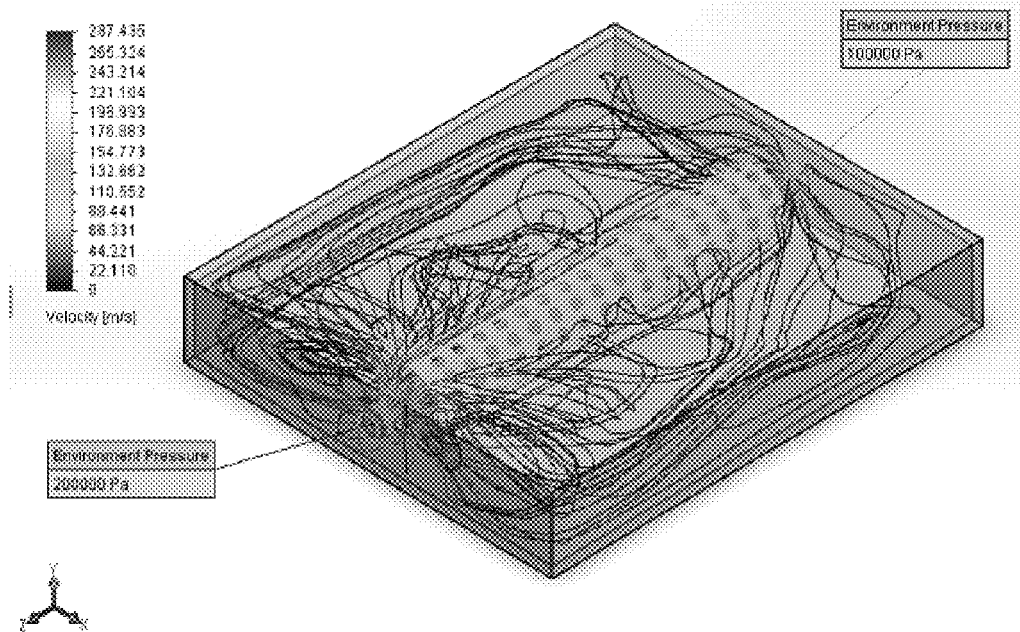

FIGS. 7G and 7H show the air flow simulation results simulated with the air purification unit of FIG. 1 under the rectangular inlet and outlet system and the circular inlet and outlet system respectively. The air purification unit of FIG. 1 was located in the direction parallel to the air flow direction.

The air flow simulation results show that the flow velocity simulated with the air purification units of the present invention is similar to that of the prior art, illustrating that the drag coefficients among the air purification units of the present invention and that of the prior art are similar, deducing that both of them also have similar air resistance. Consequently, the air purification units of the present invention provide larger surface area due to the fin structure, but still retain air resistance similar to that of the prior art.

Figure 8:
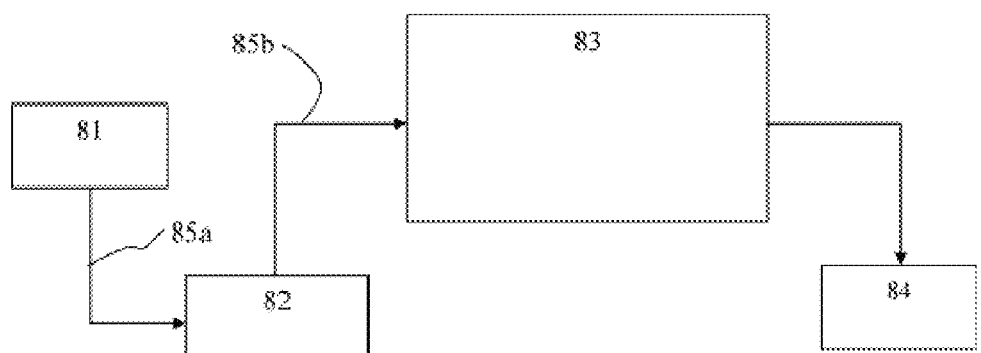
FIG. 8 is a schematic diagram showing an experimental setup of a volatile organic compound removal test according to an embodiment of the presently claimed invention.

A volatile organic compound (VOC) removal test was conducted. The experimental set-up is shown in FIG. 8. An air pump 81 pumped air into a formaldehyde source chamber 82 through an air duct 85a for generating an air flow containing formaldehyde. The air flow passed into a gas-tight chamber 83 through another air duct 85b and the inlet of the gas-tight chamber 83. Inside the gas-tight chamber 83, there was the air purification unit of FIG. 3 for removing formaldehyde. A VOC meter 84 was connected to the outlet of the gas-tight chamber 83 to monitor the concentration of formaldehyde at the outlet of the gas-tight chamber 83. An initial concentration of formaldehyde ($C_0$) was measured before switching on the UV lamp of the air purification unit. After switching on the UV lamp, concentrations of formaldehyde (C) were continuously monitored with time. A control experiment was conducted by using the air purification unit of FIG. 1. The total surface areas, provided for photocatalyst coating, of the air purification unit of FIG. 3 and of the air purification unit of FIG. 1 were about 2610 $cm^2$ and 440 $cm^2$ respectively.

For the experimental conditions, the temperature was about 20° C., the humidity was about 40%, the air flow rate was about 10 L/m and the VOC used in the test comprised about 99.9% formaldehyde.

Figure 9:
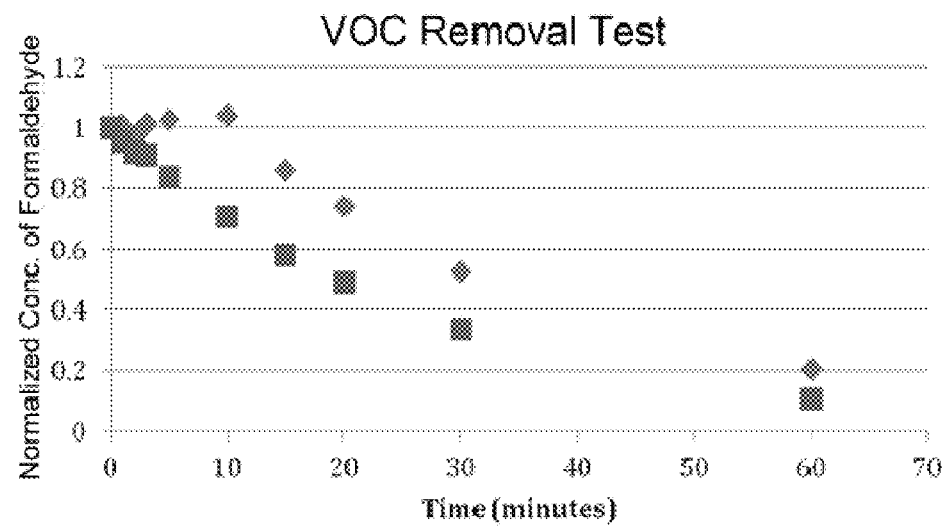
FIG. 9 is a graph showing the results of the volatile organic compound removal test according to an embodiment of the presently claimed invention.

FIG. 9 is a graph showing the results of the VOC removal test. Normalized concentrations of formaldehyde, defined as $C/C_0$, are plotted with time. The square marks represent the normalized concentrations of formaldehyde under the presence of the air purification unit of FIG. 3, and the rhombus marks represent the normalized concentrations of formaldehyde under the presence of the control design.

As shown in FIG. 9, the formaldehyde removal rate of the air purification unit of FIG. 3 is higher than that of FIG. 1, illustrating that the fin structure of present invention provides more surface areas for photocatalytic oxidation, resulting in higher VOC removal rate.

Figure 10:
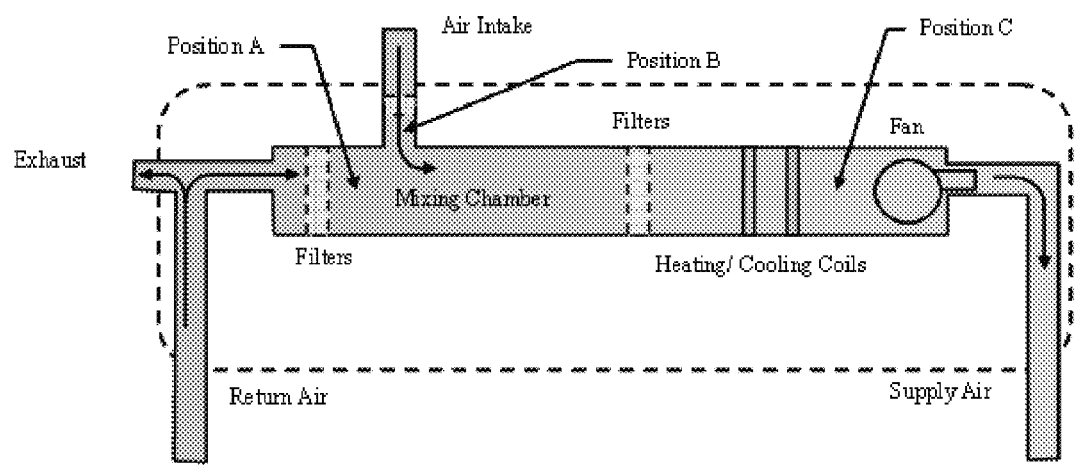
FIG. 10 shows a HVAC system indicating the possible installation locations of the air purification unit of the presently claimed invention.

FIG. 10 shows a HVAC system indicating the possible installation locations of the air purification unit of the presently claimed invention. The air purification unit of the present invention can be installed after the filters as shown in Position A, after air intake as shown in Position B, or after heating/cooling coils as shown in the Position C.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. An air purification unit, comprising:
   at least one low pressure mercury lamp for emitting UV light with wavelengths ranging from 240 to 280 nm;
   at least one fin structure, comprising a plurality of fins having a thickness in a range of 1 mm to 2 mm, wherein the fins are positioned substantially in parallel with each other and separated from each other by empty spaces, and the fins, made form copper, are coated with at least one titanium dioxide ($TiO_2$) photocatalyst layer; and
   two fin holders used to fix positions of the fins;
   wherein the fin structure is cylindrical, in which the fins are attached radially and symmetrically on to the fin holders fixed at both ends of the fin structure;
   wherein the UV lamp is enclosed by the fin structure;
   wherein the fins coated with the $TiO_2$ photocatalyst layer are irradiated by the UV light;
   wherein a fin density of the fin structure is from 1 to 2 fins/cm;
   wherein the empty spaces occupy from 60% to 90% of cross-sectional area of the fin structure; and
   wherein each of the copper fins coated with the $TiO_2$ photocatalyst layer has UV light reflectance of 10% under the wavelengths ranging from 240 to 280 nm for reflecting UV light between any two of the fins within the empty space for decomposing gaseous pollutants on the $TiO_2$ photocatalyst layer.

2. The air purification unit of claim 1, wherein the fin structure is produced by milling and welding.

3. The air purification unit of claim 1, wherein the UV lamp is a low pressure mercury lamp.

4. The air purification unit of claim 1, wherein the fin density is 1.5 fins/cm.

* * * * *